United States Patent
Kiani et al.

(10) Patent No.: US 8,777,634 B2
(45) Date of Patent: Jul. 15, 2014

(54) MAGNETIC CONNECTOR

(71) Applicants: Massi Joe E. Kiani, Laguna Niguel, CA (US); Marcelo M. Lamego, Coto de Caza (BR); Cristiano Dalvi, Irvine, CA (US); Hung The Vo, Garden Grove, CA (US)

(72) Inventors: Massi Joe E. Kiani, Laguna Niguel, CA (US); Marcelo M. Lamego, Coto de Caza (BR); Cristiano Dalvi, Irvine, CA (US); Hung The Vo, Garden Grove, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

(21) Appl. No.: 13/783,425

(22) Filed: Mar. 4, 2013

(65) Prior Publication Data
US 2013/0344708 A1    Dec. 26, 2013

Related U.S. Application Data

(62) Division of application No. 12/721,199, filed on Mar. 10, 2010, now Pat. No. 8,388,353.

(60) Provisional application No. 61/159,336, filed on Mar. 11, 2009.

(51) Int. Cl.
*H01R 11/30*    (2006.01)

(52) U.S. Cl.
USPC ............................................. 439/39; 439/950

(58) Field of Classification Search
USPC ...................................... 439/38, 305, 39, 950
See application file for complete search history.

(56) References Cited

U.S. PATENT DOCUMENTS

| | | | | |
|---|---|---|---|---|
| 4,838,797 A * | 6/1989 | Dodier | ............................. | 439/38 |
| 6,897,370 B2 * | 5/2005 | Kondo et al. | .................. | 136/243 |
| 7,204,695 B1 * | 4/2007 | Shiu et al. | ......................... | 439/38 |
| 7,252,565 B2 * | 8/2007 | Hunter | ........................... | 439/357 |
| 7,963,774 B2 * | 6/2011 | Shiff et al. | ........................ | 439/38 |

* cited by examiner

*Primary Examiner* — Hien Vu
(74) *Attorney, Agent, or Firm* — Glenn R. Smith; Lisa L. Smith; Law Office of Glenn R. Smith

(57) ABSTRACT

A magnetic connector has a receptacle and a plug. The receptacle has an electromagnet comprising an inner core, an outer core, a coil disposed around the inner core and an air gap defined by the edges of the inner and outer cores. The plug has a plug core and an anchor defined by the plug core edge. The anchor is configured to insert into the air gap as a receptacle socket electrically connects with plug pins. The coil is energized and de-energized so as to assist in the insertion or removal of the anchor from within the air gap and the corresponding connection and disconnection of the socket and pins.

11 Claims, 17 Drawing Sheets

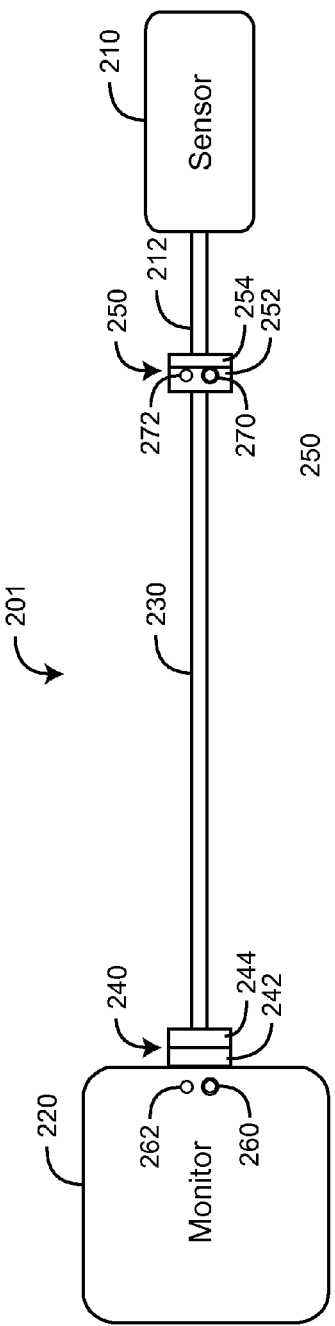
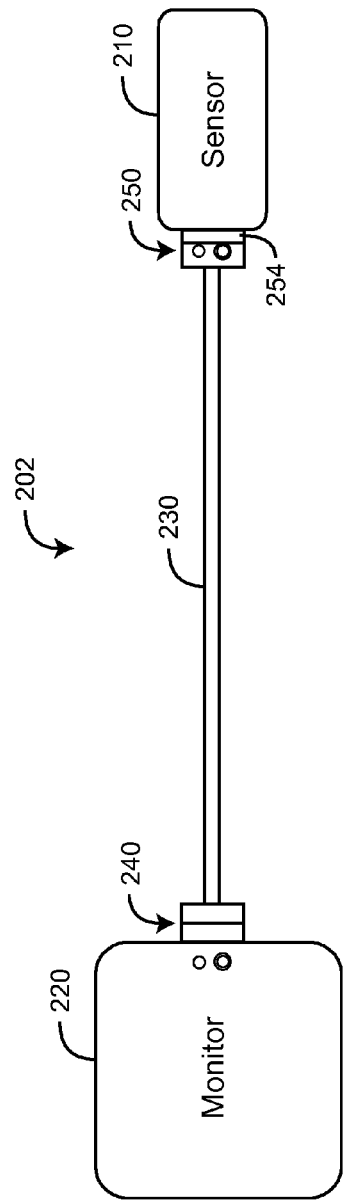
FIG. 2A
FIG. 2B

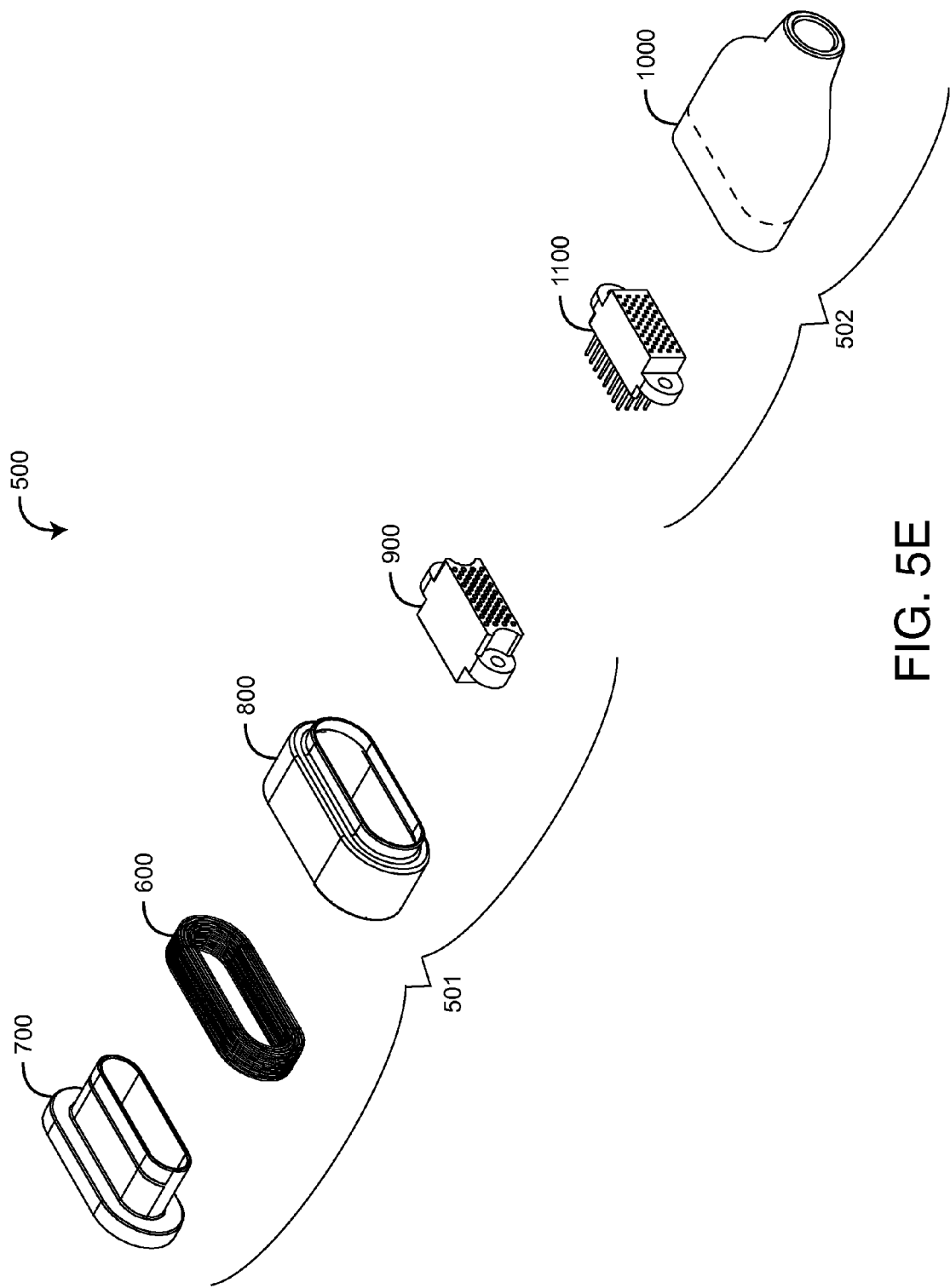

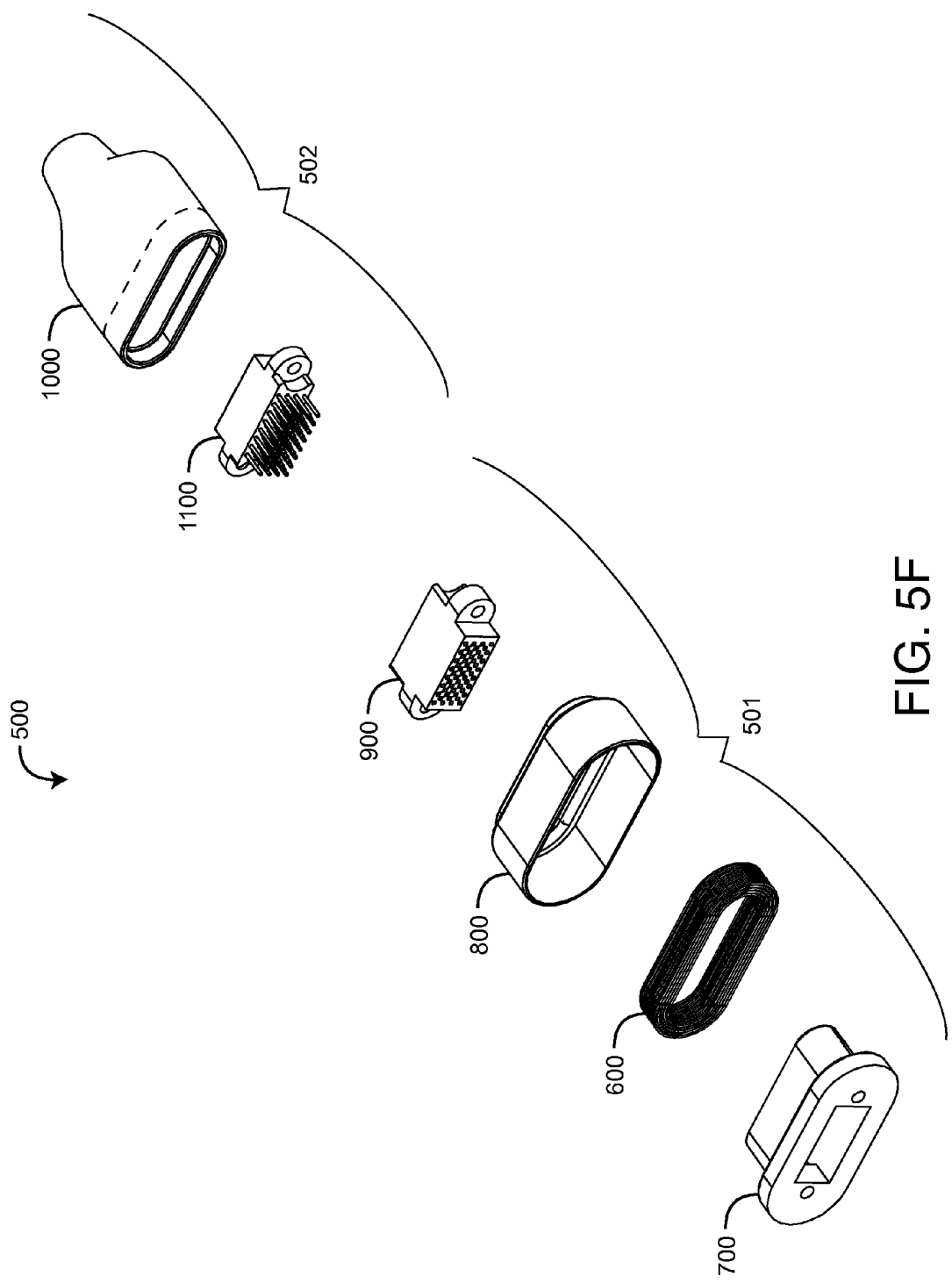

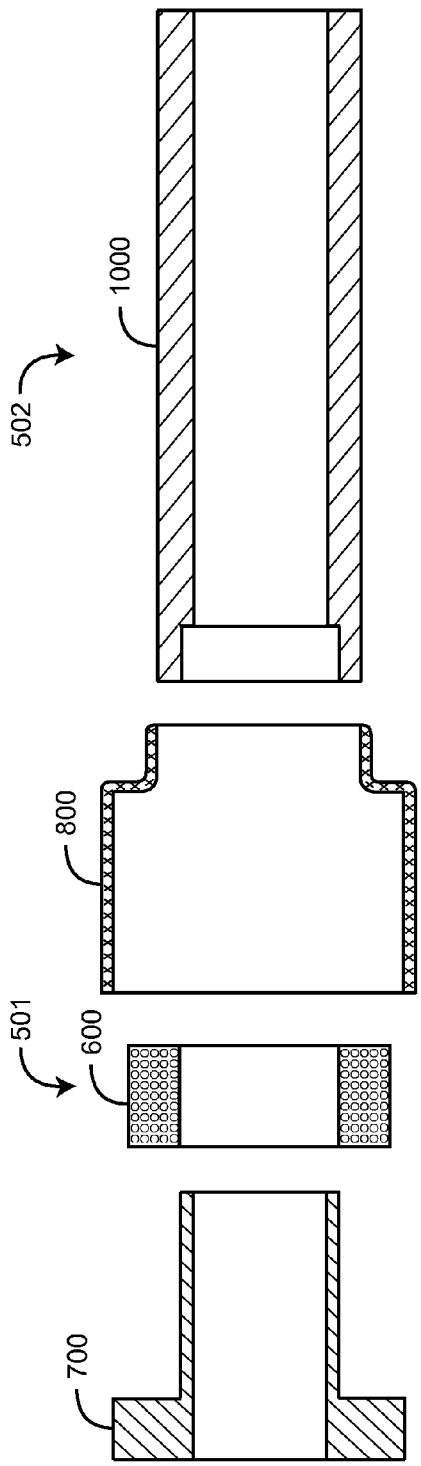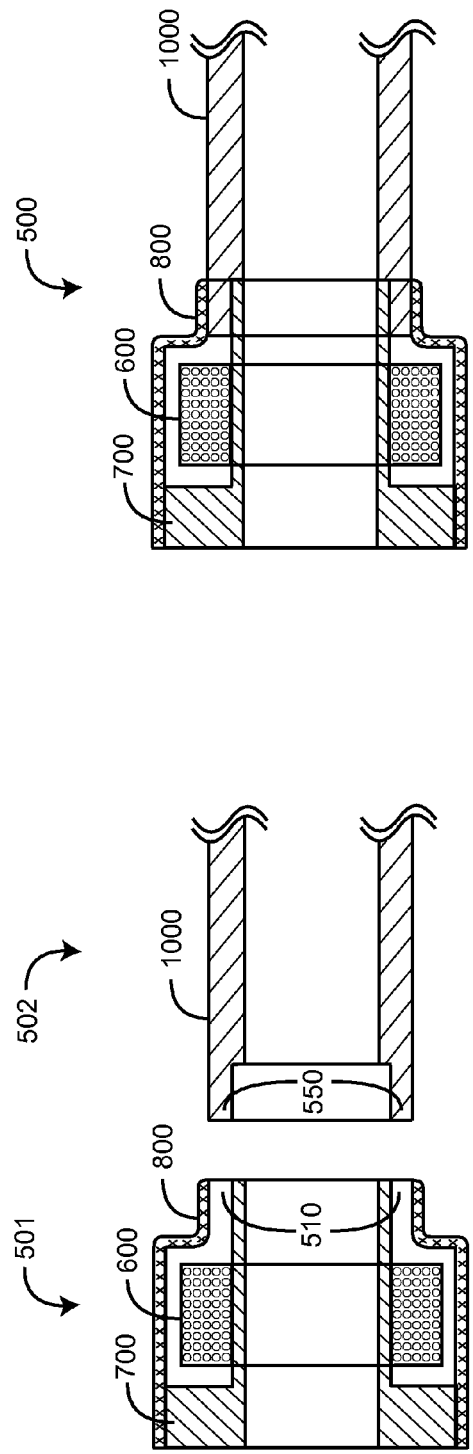
FIG. 6A
FIG. 6B
FIG. 6C

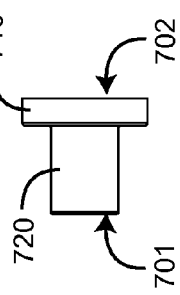
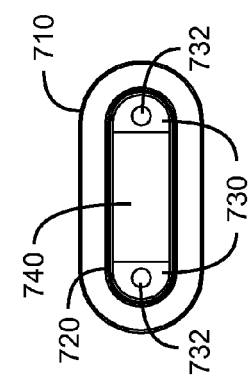
FIG. 7A
FIG. 7B
FIG. 7C
FIG. 7D

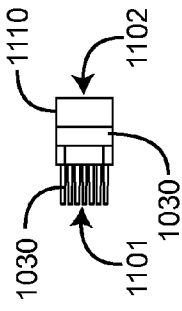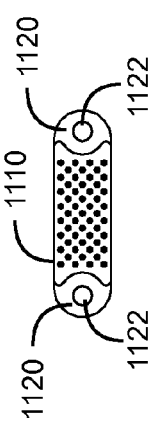

MAGNETIC CONNECTOR

CROSS-REFERENCE TO RELATED APPLICATIONS

This application is a divisional of U.S. patent application Ser. No. 12/721,199 filed Mar. 10, 2010, titled Magnetic Connector, issuing Mar. 5, 2013 as U.S. Pat. No. 8,388,353, which relates to and claims the benefit of prior U.S. Provisional Patent Application Ser. No. 61/159,336, filed Mar. 11, 2009, titled Magnetic Connector, both prior applications hereby incorporated in their entireties by reference herein.

BACKGROUND OF THE INVENTION

Noninvasive physiological monitoring systems for measuring constituents of circulating blood have advanced from basic pulse oximeters to monitors capable of measuring abnormal and total hemoglobin among other parameters. A basic pulse oximeter capable of measuring blood oxygen saturation typically includes an optical sensor, a monitor for processing sensor signals and displaying results and a cable electrically interconnecting the sensor and the monitor. A pulse oximetry sensor typically has a red wavelength light emitting diode (LED), an infrared (IR) wavelength LED and a photodiode detector. The LEDs and detector are attached to a patient tissue site, such as a finger. The cable transmits drive signals from the monitor to the LEDs, and the LEDs respond to the drive signals to transmit light into the tissue site. The detector generates a signal responsive to the emitted light after attenuation by pulsatile blood flow within the tissue site. The cable transmits the detector signal to the monitor, which processes the signal to provide a numerical readout of oxygen saturation ($SpO_2$) and pulse rate. Advanced blood parameter monitors utilizing multiple LEDs that transmit a spectrum of wavelengths incorporate pulse oximetry and the capability of additional hemoglobin, perfusion and pulse measurements such as carboxyhemoglobin (HbCO), methemoglobin (HbMet), total hemoglobin (Hbt), total hematocrit (Hct), perfusion index (PI) and pulse variability index (PVI), as a few examples.

High fidelity pulse oximeters capable of reading through motion induced noise are disclosed in U.S. Pat. Nos. 6,770,028, 6,658,276, 6,157,850, 6,002,952 5,769,785, and 5,758,644, which are assigned to Masimo Corporation ("Masimo") and are incorporated by reference herein. Advanced physiological monitors and corresponding multiple wavelength optical sensors are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Noninvasive blood parameter monitors and corresponding multiple wavelength optical sensors, such as Rainbow™ adhesive and reusable sensors and RAD57™ and Radical-7™ monitors are also available from Masimo.

SUMMARY OF THE INVENTION

Advanced physiological monitoring systems utilize a significant number of control and signal lines, creating a high pin density for sensor, cable and monitor connectors. This high pin density places a heavy demand on the connector mechanisms with respect to connect/disconnect ease, connection integrity, connector cost and life. A magnetic connector advantageously utilizes one or more of electromagnets, permanent magnets, magnetically permeable materials and air gaps to auto-align, attach, hold and release connectors for physiological monitoring applications.

One aspect of a magnetic connector is a receptacle and a plug. The receptacle has a wiring end, a receptacle contact end, a receptacle core, a coil and a receptacle contact set. The plug has a cable end, a plug contact end, a plug core and a plug contact set. An air gap is located in the receptacle core at the receptacle contact end. The coil, the core and the air gap form a magnetic circuit so that energizing the coil creates a magnetic field in the air gap. An anchor extends from plug core at the plug contact end so as to fit within the air gap. The receptacle contact set and the plug contact set electrically connect as the anchor inserts into the air gap.

In various embodiments, the receptacle core has an inner core and an outer core. The coil is wrapped around the inner core. The inner core and the outer core have concentric elongated circular receptacle edges that define the air gap. The plug core has an elongated circular plug edge that defines the anchor. The receptacle contact set has a socket block with contact apertures and contacts at least partially disposed within the contact apertures. The plug contact set has a pin block with pin apertures and pins at least partially disposed within the pin apertures. The pins insert into the contacts.

Additional embodiments include at least one permanent magnet disposed in either the anchor or the air gap or both. Power leads transmit current from a power source to the coil. A switch in series with one of the power leads is actuated either to block current in the power leads and de-energize the coil or to pass current in the power leads and energize the coil. An LED in series with one of the power leads illuminates according to the flow of current in the power leads so as to indicate if the coil is energized.

Another aspect of a magnetic connector involves interconnecting an optical sensor and a physiological monitor with a magnetic connector having a monitor receptacle and a cable plug. A receptacle core and a plug core are each constructed of magnetically permeable material. Receptacle contacts are housed within the receptacle core, and plug contacts are housed within the plug core. The receptacle core and the plug core are interconnected so as to electrically connect the receptacle contacts and the plug contacts. The receptacle core and the plug core are also magnetically coupled so as to maintain the interconnection. In an embodiment, a coil is wrapped around either the receptacle core or the plug core so as to form an electromagnet. An air gap is formed in the electromagnet core and an anchor is formed to extend from the other core. The anchor fits within the air gap. Current to the coil is switched on or off so that the electromagnet assists in locking the anchor within the air gap or releasing the anchor from the air gap.

In various embodiments, at least one permanent magnet is embedded within one of the cores. If a permanent magnet is embedded within or near the anchor or near the air gap, then the permanent magnet locks the anchor within the air gap when the coil is de-energized. When the coil is energized, it creates an opposing field to the permanent magnet within the air gap so as to release the anchor. This permanent-magnet-based magnetic coupling holds the receptacle and plug together when the coil is de-energized, but allows the receptacle and plug to be easily disconnected by briefly energizing the coil.

A further aspect of a magnetic connector is first and second magnetic elements having first and second contact sets. The first contact set is housed proximate the first magnetic element, and the second contact set is housed proximate the second magnetic element. At least one of the magnetic elements is responsive to a current input so as to alter a magnetic coupling between the magnetic elements. The magnetic coupling assists in making or breaking an electrical connection between the first and second contact sets. In an embodiment, the first magnetic element comprises a core of magnetically permeable material, a conductive coil having "N" turns disposed around at least a portion of the core, coil leads in communications with a current source and an air gap defined within the core. The current source has "I" amps energizing the coil so as to generate a electromagnetic field within the air gap proportional to N times I. In an embodiment, the second magnetic element comprises an anchor of magnetically permeable material sized to closely fit within the air gap. The contact sets make an electrical connection as the anchor is manually inserted into the air gap and break an electrical connection as the anchor is manually withdrawn from the air gap. The anchor locks within the air gap in response to a magnetic field within the air gap so as to maintain an electrical connection between the contact sets.

In various other embodiments, a switch in series with the coil controls whether the coil is energized, and an LED in series with the switch indicates whether the coil is energized. A permanent magnet is incorporated within the first magnetic element near the air gap and/or within the second magnetic element in or near the anchor. The permanent magnet has poles oriented so that its magnetic field opposes the air gap field.

In yet another embodiment, a magnetic connector has a plug means and a corresponding receptacle means for interconnecting a sensor and a corresponding monitor. The magnetic connector also has a socket means and a corresponding pin means housed within the plug means and the receptacle means for making and breaking electrical communications between sensor conductors and monitor conductors as the plug is inserted into and removed from the receptacle, respectively. Further, the magnetic connector has a pair of mating magnetic element means housed within the plug means and the receptacle means for assisting in at least one of the making and breaking of electrical communications between the socket means and the pin means. In an embodiment, the mating magnetic element means comprises an electromagnet means for generating a magnetic field within an air gap and an anchor means for locking within and releasing from the air gap according to power provided to the electromagnet means. Various other embodiments include a permanent magnet means for opposing the air gap magnetic field disposed proximate at least one of the air gap and the anchor means, a switch means for manually controlling the air gap magnetic field so as to secure or release the anchor means within the air gap and/or an indicator means for visually identifying the state of the air gap magnetic field.

DESCRIPTION OF THE DRAWINGS

FIGS. 2A-D are illustrations of different magnetic connector configurations for connecting a sensor and a monitor;

FIGS. 5A-F are front and back, perspective and exploded, connected and disconnected views of a magnetic connector receptacle and plug;

FIGS. 6A-E are cross sectional exploded, disconnected, connected and detailed views of receptacle and plug core assemblies;

FIGS. 7A-D are top, perspective, front and side views, respectively, of a receptacle inner core;

FIGS. 9A-D are top, perspective, front and side views, respectively, of a receptacle contact set;

FIGS. 11A-D are top, perspective, front and side views, respectively, of plug contact set.

DETAILED DESCRIPTION OF THE PREFERRED EMBODIMENTS

Figure 1:
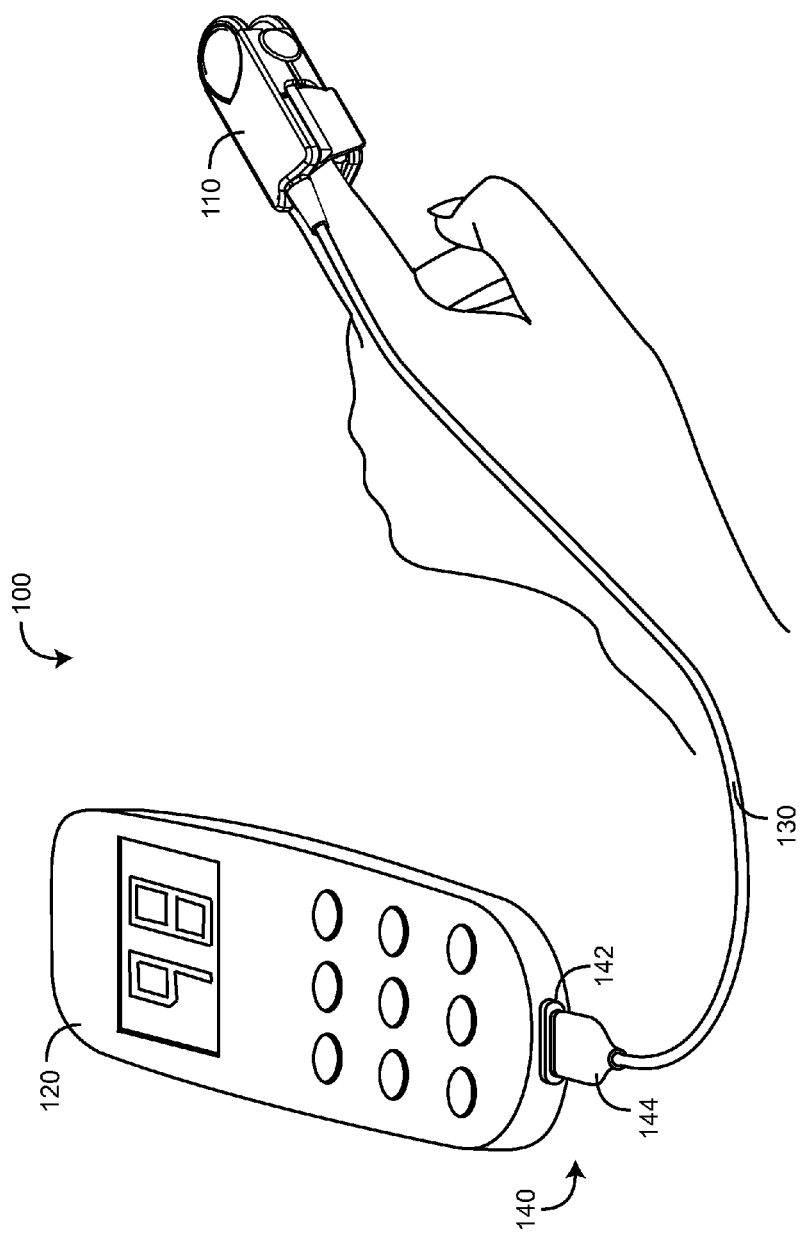
FIG. 1 is a perspective view of a physiological monitoring system having a magnetic connector.

FIG. 1 illustrates a physiological monitoring system 100 having a sensor 110, a monitor 120, a cable 130 interconnecting the sensor 110 and the monitor 120, and a magnetic connector 140. The magnetic connector 140 has a receptacle 142 mounted in the monitor 120 and a plug 144 terminating the cable 130. Advantageously, the magnetic connector 140 utilizes magnetic fields generated by combinations of electromagnets, permanent magnets, magnetically permeable materials and air gaps to auto-align, attach, hold and release the receptacle 142 and plug 144. In this manner, a relatively small connector having the high contact density needed for advanced physiological monitoring applications can be made to have ease of use, durability and low cost characteristics. These characteristics are particularly important for handheld monitoring applications. Various combinations of sensor 110, monitor 120, cable 130 and magnetic connector 140 are described with respect to FIGS. 2A-D, below.

Figure 2C:
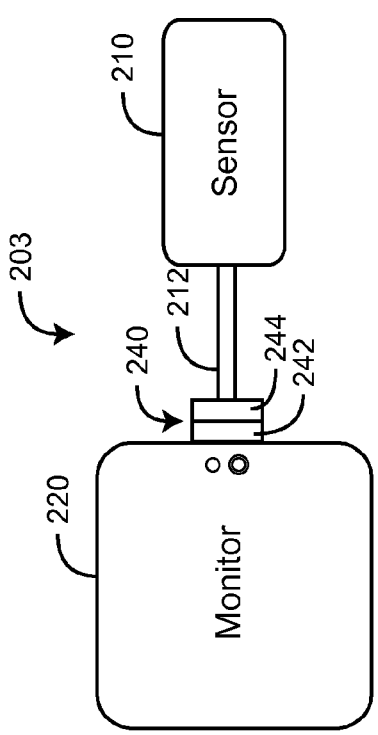
Figure 2D:
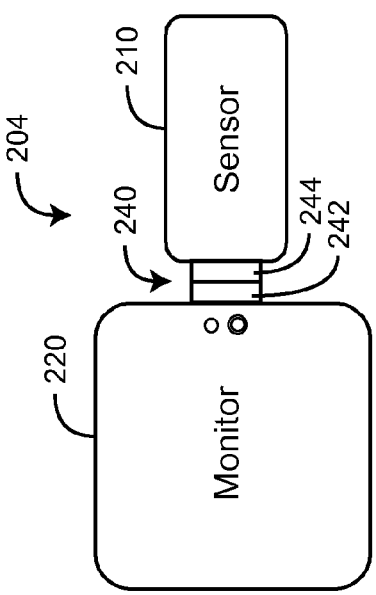

FIGS. 2A-D illustrate different configurations of one or more magnetic connectors 240, 250 utilized to connect a sensor 210 and a monitor 220. FIGS. 2A-B illustrate dual magnetic connector configurations and FIGS. 2C-D illustrate single magnetic connector configurations. As shown in FIG. 2A, in a first configuration, a sensor 210 is connected to a monitor 220 via a patient cable 230 and a sensor cable 212. The patient cable 230 is a standalone component and the sensor cable 212 is integral to the sensor 210. A first magnetic connector 240 is disposed proximate the monitor 220 for connecting the patient cable 230 to the monitor 220. A second magnetic connector 250 is disposed between the patient cable 230 and the sensor cable 212 for connecting the patient cable 230 to the sensor 210.

In particular, the first magnetic connector 240 has a receptacle 242 mounted to the monitor 220 and a plug 244 mounted to one end of the patient cable 230. A magnetic field provides at least some force for assisting a person to join and/or disjoin the receptacle 242 and plug 244 so as to electrically connect and/or disconnect patient cable 230 conductors and monitor 220 conductors. The monitor 220 has a button 260 that is actuated so as to energize/de-energize the magnetic field in the receptacle 242. The monitor 220 also has an indicator light 262 that signals the magnetic field status as on or off.

Similarly, the second magnetic connector 250 has a receptacle 252 mounted to one end of the patient cable 230 and a plug 254 mounted to the end of the sensor cable 212. Likewise, a magnetic field provides at least some force for assisting a person to join and/or disjoin the receptacle 252 and plug 254 so as to electrically connect and/or disconnect patient cable 230 conductors and sensor cable 212 conductors. Also, the patient cable receptacle 252 has a button 270 so as to energize/de-energize the magnetic field in the receptacle 252 and an indicator light 272 that signals the magnetic field status as on or off. A magnetic connector embodiment including a receptacle and a plug are described with respect to FIGS. 5-11, below.

As shown in FIG. 2B, in a second configuration, a sensor 210 is connected to a monitor 220 via a patient cable 230. A first magnetic connector 240 is disposed proximate the monitor 220 and a second magnetic connector 250 is disposed proximate the sensor 210 for interconnecting the sensor 210 and the monitor 220 via the sensor cable 230. The first magnetic connector 240 is as described with respect to FIG. 2A, above. The second magnetic connector 250 is as described with respect to FIG. 2A, above, except that the plug portion 254 is disposed proximate the sensor 210.

As shown in FIG. 2C, in a third configuration, a sensor 210 is connected to a monitor 220 via a sensor cable 212. A single magnetic connector 240 is disposed proximate the monitor 220 for connecting the monitor 220 to the sensor 210 via the sensor cable 212. The magnetic connector 240 has a receptacle 242 mounted to the monitor 220 and a plug 244 mounted to the end of the sensor cable 212 for interconnecting the sensor 210 and the monitor 220. Otherwise, the magnetic connector 240 is as described with respect to FIG. 2A, above.

As shown in FIG. 2D, in a fourth configuration, a sensor 210 is connected directly to a monitor 220. A single magnetic connector 240 is disposed between the monitor 220 and sensor 210. In particular, the magnetic connector 240 has a receptacle 242 disposed proximate the monitor 220 and a plug 244 disposed proximate the sensor 210. Otherwise, the magnetic connector 240 is as described with respect to FIG. 2A, above.

As described with respect to FIGS. 2A-D, a monitor 220 may be, as examples, any of a multi-parameter patient monitoring system (MPMS), a plug-in to a MPMS, a standalone monitor, a handheld monitor, a handheld monitor docked to a docking station, a personal monitoring device or any physiological parameter calculating device that processes one or more sensor signals to derive a physiological measurement. As described above, a sensor 210 may be a reusable, resposable or disposable sensor; an optical transmission or reflection sensor; a blood pressure sensor; a piezo-electric or other acoustic sensor; an assembly of EKG or EEG electrodes; or any non-invasive or invasive device for providing physiological signals to a monitoring or calculating device.

Figure 3:
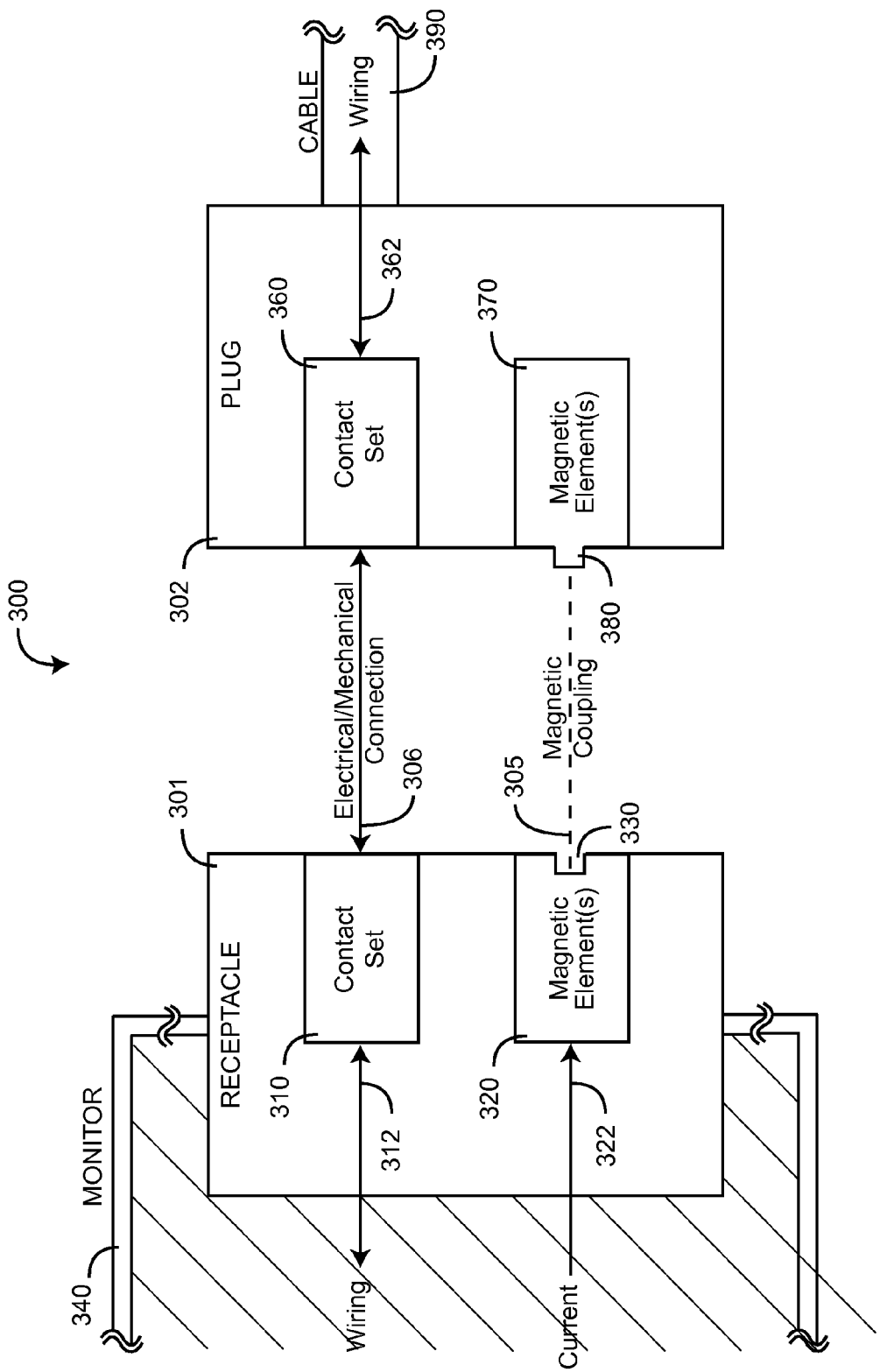
FIG. 3 is a general block diagram of a magnetic connector.

FIG. 3 generally illustrates a magnetic connector 300 having a receptacle 301 and a plug 302. The receptacle 301 has a contact set 310 and magnetic element(s) 320. The plug 302 has a contact set 360 and magnetic element(s) 370. The magnetic element pair 320, 370 provides a magnetic coupling 305 between receptacle 301 and plug 302. This magnetic coupling assists a user in making or breaking the electrical/mechanical connection between the contact sets 310, 360, making or breaking continuity between receptacle wiring 312 and plug wiring 362. In a particularly advantageous embodiment, the receptacle magnetic element(s) 320 incorporate an electromagnet. When energized by a current source 322, the electromagnet generates a magnetic field within an air gap 330 so as to attract or repel a corresponding anchor 380 that closely fits within the air gap 330. In various embodiments, the magnetic elements 320, 370 may include one or more of electromagnets, permanent magnets, materials with high magnetic permeability, air gaps and anchors. In various embodiments, the receptacle or plug may be integrated with a monitor, such as mounted to a monitor chassis, or attached to a sensor cable or patient cable, for example.

Figure 4A:
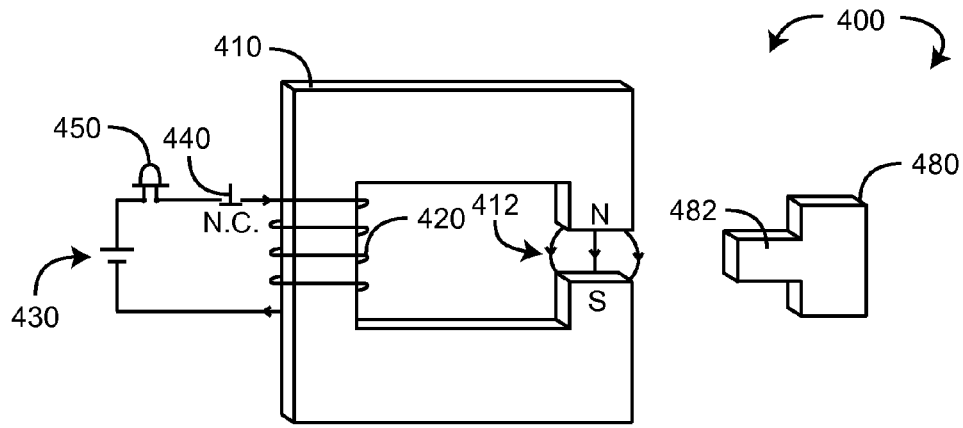
FIGS. 4A-C are illustrations of various magnetic coupling mechanisms incorporated within a magnetic connector.
Figure 4B:
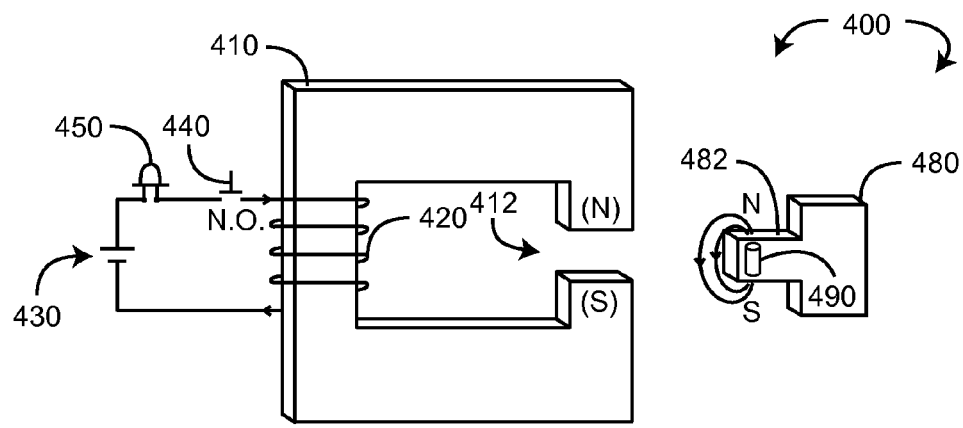
Figure 4C:
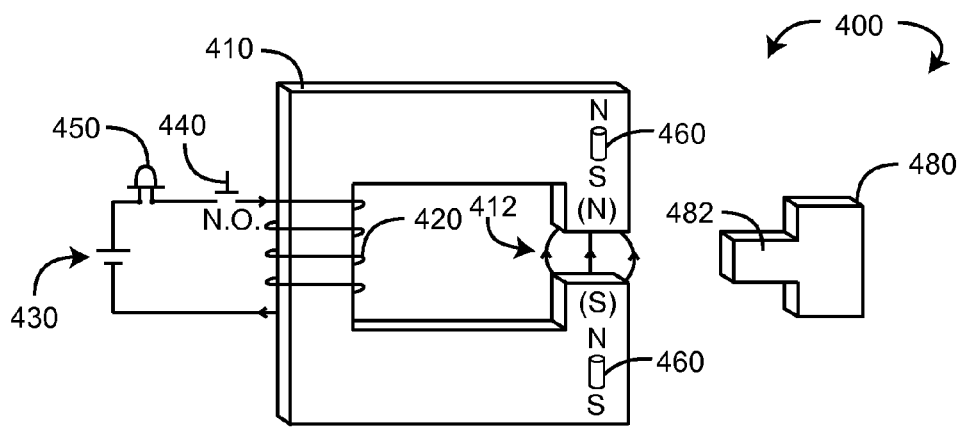

FIGS. 4A-C generally illustrate various magnetic coupling 305 (FIG. 3) embodiments between the receptacle and plug of a magnetic connector, such as generally described above with respect to FIG. 3. These embodiments include a receptacle core 410 defining an air gap 412 and a corresponding plug core 480 defining an anchor 482. An electromagnet is formed from the receptacle core 410, a coil 420, a DC current source 430, a switch 440 and an indicator 450. When the switch 440 is closed, the coil 420 is energized, the indicator 450 is on and the electromagnet generates a magnetic field within the air gap 412. When the switch 440 is opened, the coil 420 is de-energized, the indicator 450 is off and the air gap magnetic field is extinguished. The receptacle core 410 and plug core 480 are constructed of materials having a high magnetic permeability. A substantial magnetic field is created in the air gap 412 having north "N" and south "S" polarities as shown. The receptacle core 410 and plug core 480 can be any of a variety of shapes and sizes. For example, the embodiment described below with respect to FIGS. 5-11 utilizes a receptacle core that defines an elongated, circular air gap and a plug core that defines a corresponding elongated, circular anchor.

As shown in FIG. 4A, in a first embodiment, the plug core 480 or at least the anchor 482 is a soft iron material and the switch 440 is normally closed (N.C.). Accordingly, D.C. current normally flows in the coil 420 and a magnetic field is maintained in the air gap 412. As such, the anchor 482 is attracted to and held within the air gap 412, locking the corresponding plug (not shown) to the corresponding receptacle (not shown). The switch 440 is actuated to interrupt the D.C. current, which releases the anchor 482 from the air gap 412 and allows the plug to be pulled from the receptacle.

As shown in FIG. 4B, in a second embodiment, the plug core 480 is a permanent magnet or is a material with a high magnetic permeability embedded with one or more permanent magnets 490. The permanent magnet field attracts the anchor 482 to the air gap 412, so as to lock a corresponding plug to a corresponding receptacle. The switch 440 is normally open (N.O.). Accordingly, actuating the switch 440 pulses the D.C. current to the coil 420, temporarily creating an opposing field (N), (S) within the air gap 412. This releases the anchor 482 from the air gap 412 and allows the plug to be pulled from the receptacle.

As shown in FIG. 4C, in a third embodiment, the plug core 480 is a soft iron material. One or more permanent magnets 460 are embedded within the receptacle core 410. The permanent magnet field attracts the anchor 482 to the air gap 412, so as to lock a corresponding plug to a corresponding receptacle. The switch 440 is normally open (N.O.). Accordingly, actuating the switch 440 pulses the D.C. current to the coil 420, temporarily creating an opposing field (N), (S) within the air gap 412. This releases the anchor 482 from the air gap 412 and allows the plug to be pulled from the receptacle.

FIGS. 5A-F illustrate a magnetic connector embodiment 500 having a receptacle 501 and a plug 502. The receptacle 501 is mountable to a device, such as a physiological monitor. The plug 502 is attachable to a sensor cable or a patient cable. The receptacle 501 has a core 700, 800 (FIGS. 5E-F) that defines an elongated circular air gap 510. The plug 502 has a core 1000 (FIGS. 5E-F) that defines an elongated circular anchor 550, which inserts within the air gap 510. The receptacle core 700, 800 and corresponding coil 600 (FIGS. 5E-F) form an electromagnet that, when energized, generates a magnetic field within the air gap 510. Depending on the configuration, the electromagnetic field holds or releases the anchor 550 from the air gap 510 so as to lock or unlock the connection between the receptacle 501 and plug 502.

Also shown in FIGS. 5A-F, the receptacle 501 has a receptacle contact set 900 and the plug 502 has a plug contact set 1100. When the receptacle 501 and plug 502 are connected, the plug contact set 1100 inserts into the receptacle contact set 900, electrically coupling the receptacle 501 and socket 502.

Figure 5A:
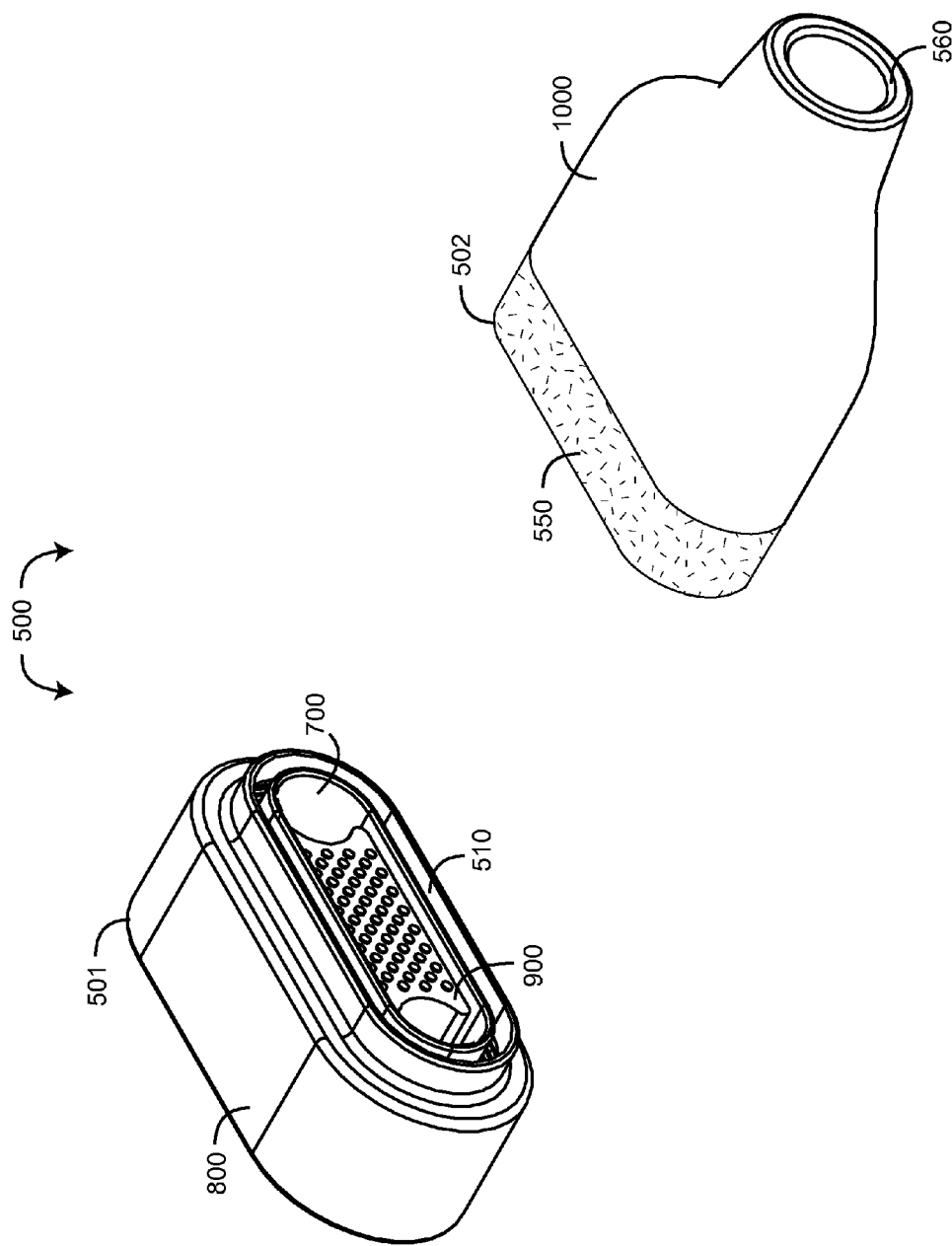
Figure 5B:
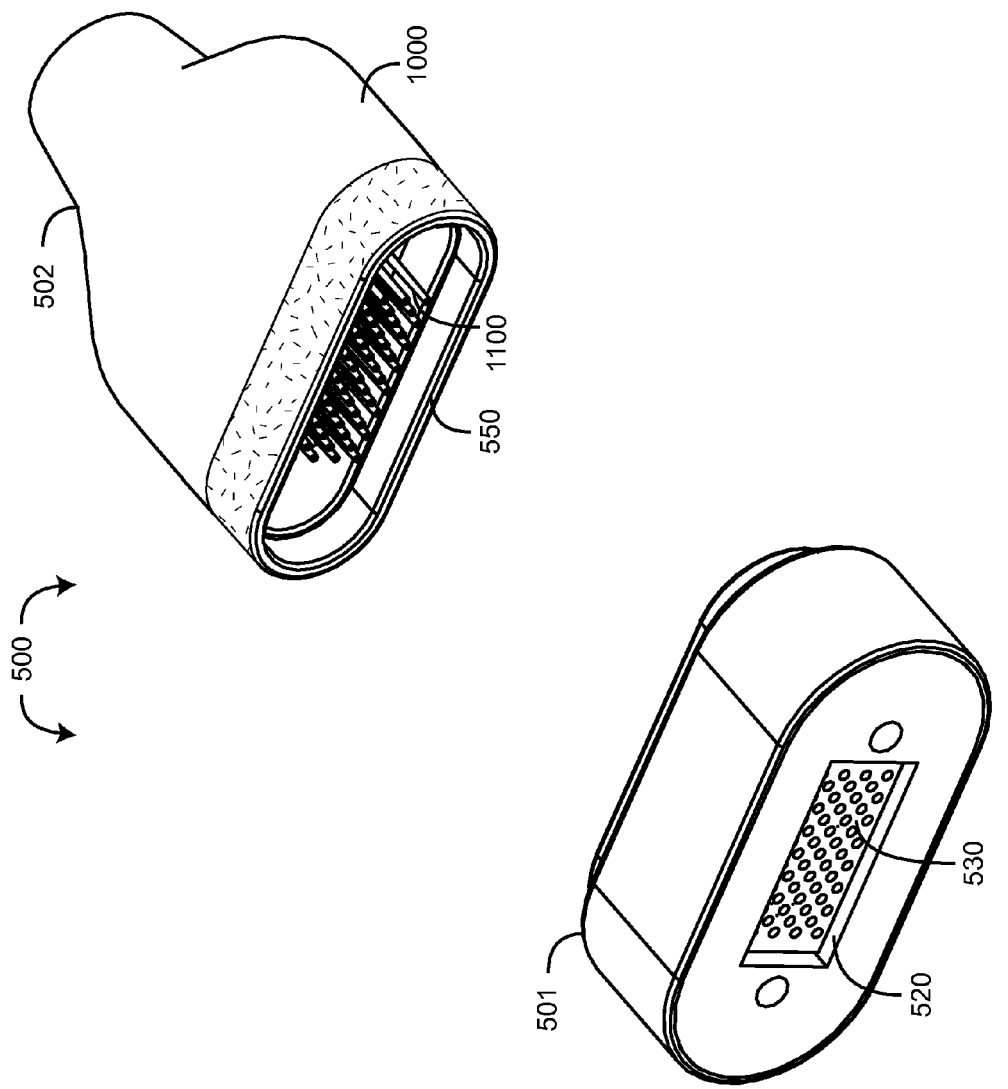
Figure 5D:
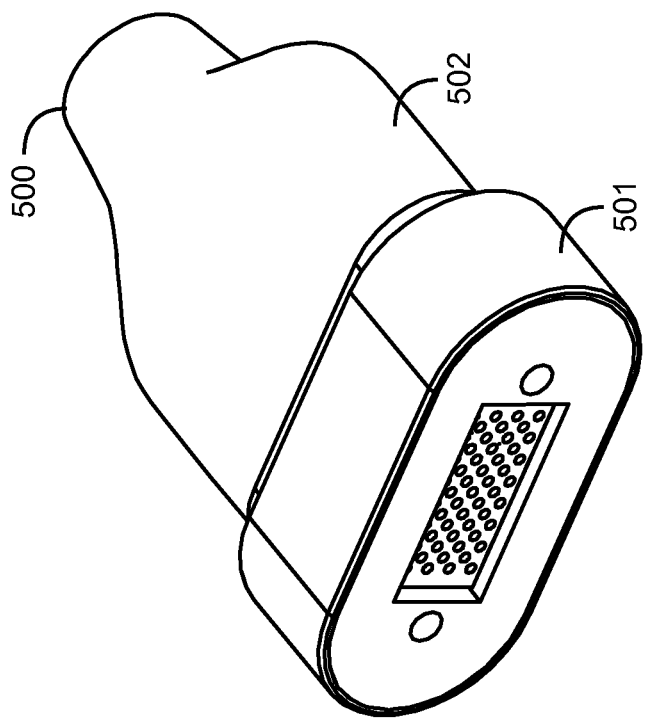
Figure 5C:
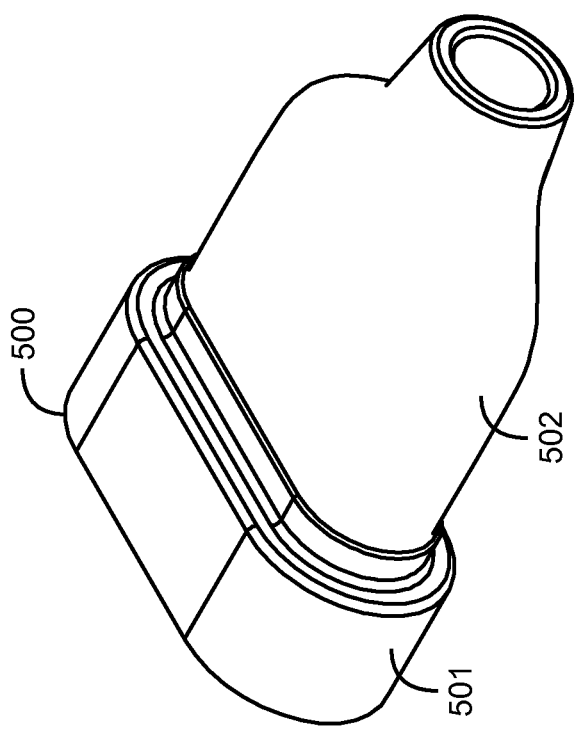

This electrical coupling provides an electrical path between cable conductors attached to the plug 502 at a cable end 560 (FIG. 5A) and wires attached to the receptacle 501 at a device end 530 (FIG. 5B).

As shown in FIGS. 5E-F, the receptacle 501 has a coil 600, an inner core 700, an outer core 800 and a contact set 900. The receptacle core 700, 800 forms a receptacle housing. In particular, the coil 600 is wound around the inner core 700 and enclosed by the outer core 800. The contact set 900 is mounted inside the inner core 700. The plug 502 has a core 1000 and a contact set 1100. The plug core 1000 forms a plug housing, and the contact set 1100 is mounted inside the plug core 1000.

Figure 6E:
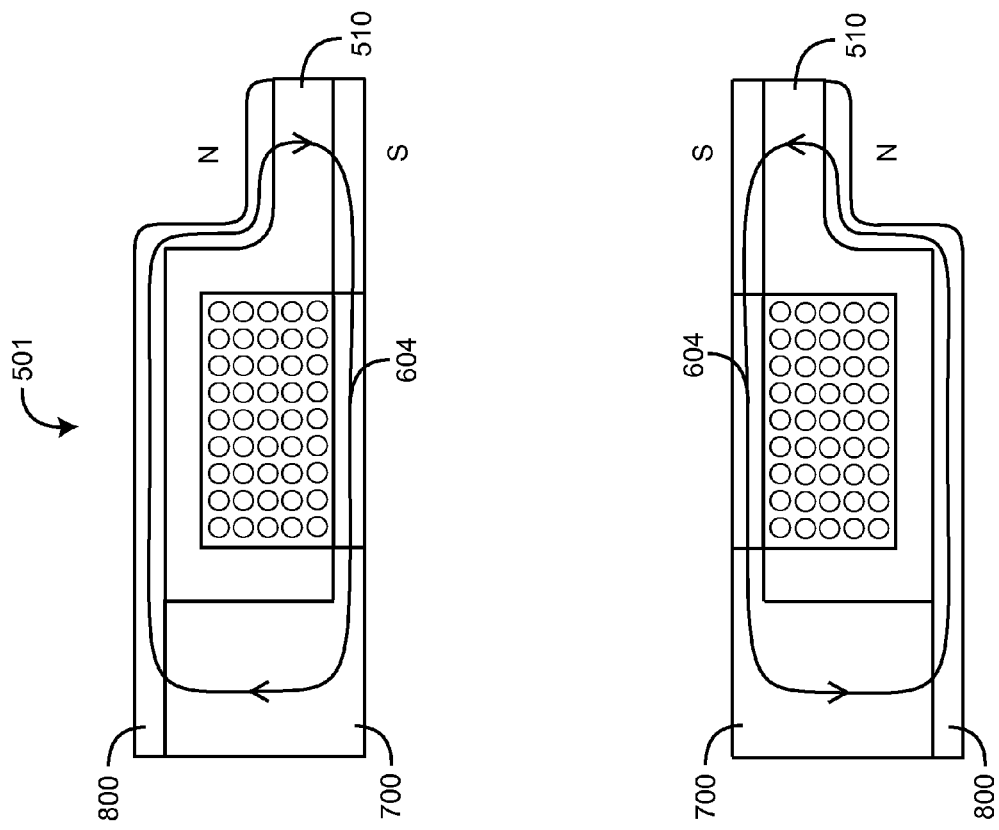
Figure 6D:
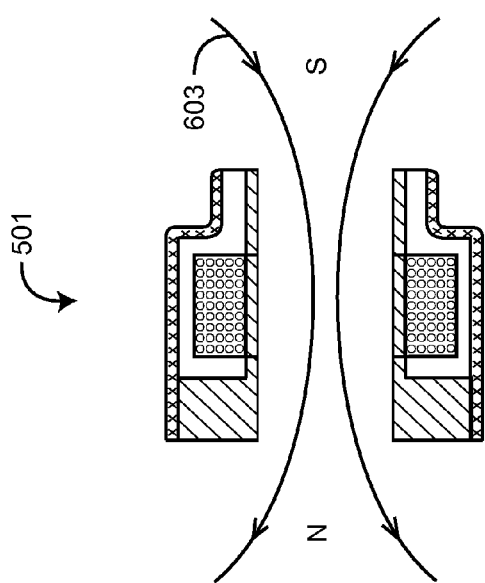
Figure 8B:
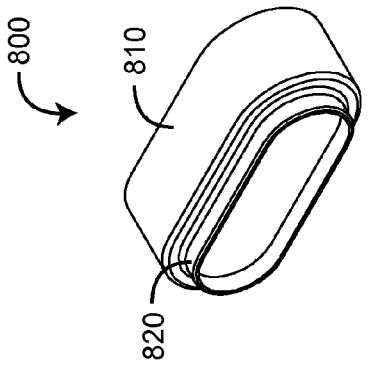
FIGS. 8A-D are top, perspective, front and side views, respectively, of a receptacle outer core.
Figure 8D:
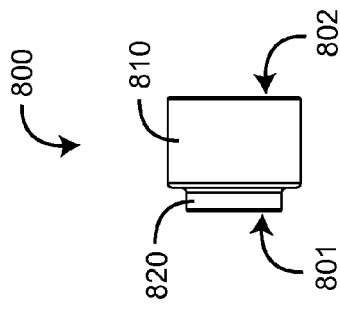
Figure 8A:
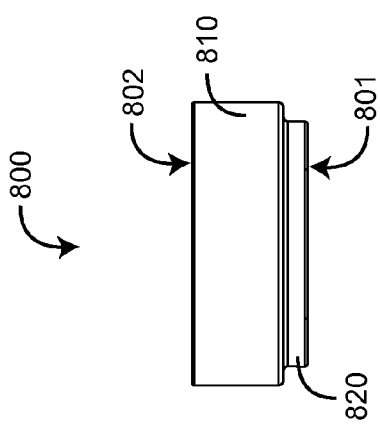
Figure 8C:
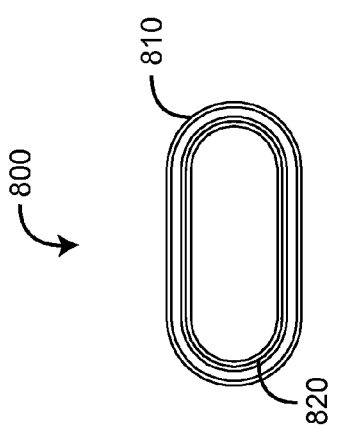
Figure 10A:
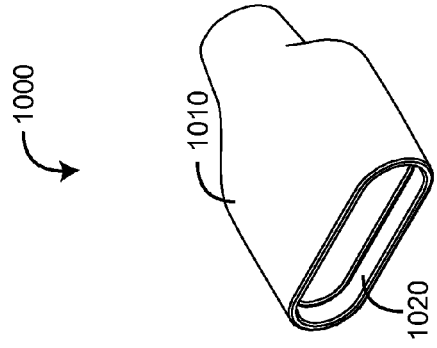
FIGS. 10A-D are top, perspective, front and side views, respectively, of a plug core.
Figure 10B:
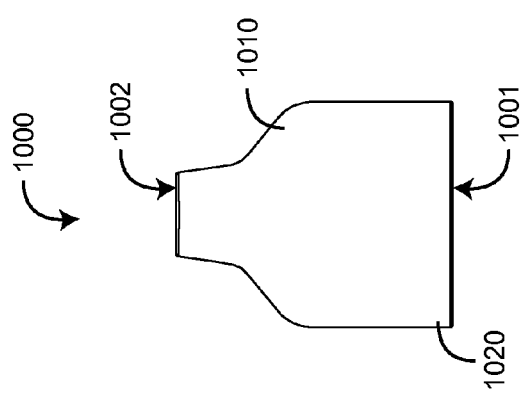
Figure 10C:
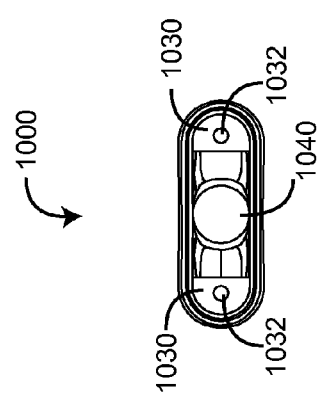
Figure 10D:
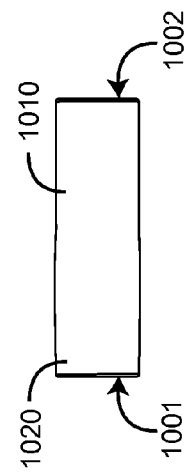

FIGS. 6A-E are cross-sections of the receptacle core 700, 800 and plug core 1000. As shown in FIGS. 6A-C, the coil 600 is wound around the receptacle inner core 700 and enclosed by the outer core 800. Thus configured, the front edges of the receptacle core 700, 800 form an air gap 510. Likewise, the front edge of the plug core 1000 forms an anchor 550 that inserts (FIG. 6C) into the air gap 510. As shown in FIG. 6D, if DC current flows in the top-half of the coil in a direction into the page and in the bottom-half of the coil in a direction out of the page, then the magnetic field 603 produced by the coil has a north pole, N, at the left and a south pole, S, at the right (right-hand rule). As shown in FIG. 6E, the magnetic flux 604 in the receptacle core resulting from the magnetic field 603 is mostly confined within the walls of the receptacle core 700, 800, and results in a magnetic field in the air gap 510 as shown. As a result, the magnetic field in the air gap 510 has a north pole at the outer core portion and a south pole at the inner core portion. Thus, a "slice" of the receptacle core 700, 800 and corresponding air gap 510 are analogous to the core and air gap described with respect to FIGS. 4A-C, above. Likewise, a "slice" of the plug core 1000 and plug anchor 550 are analogous to the plug core and anchor described with respect to FIGS. 4A-C, above.

FIGS. 7-11 illustrate further details of the receptacle inner core 700, outer core 800, receptacle contact set 900, plug core 1000 and plug contact set 1100. As shown in FIGS. 7A-D, the receptacle inner core 700 mounts the receptacle contact set 900 (FIGS. 9A-D), supports the coil 600 (FIGS. 5E-F), and defines a portion of the receptacle core air gap 510 (FIG. 5A). The inner core 700 has a planar base 710 defining a back side 702 and a tubular coil support 720 extending from the base 710 and defining a front side 701. Both the base 710 and the coil support 720 have an elongated, circular cross-section. Inside the coil support 720 is a bracket 730 and corresponding bracket holes 732 for mounting the receptacle contact set 900 (FIGS. 9A-D). A wiring aperture 740 provides wiring access to the contact set 900 from the back side 702. An elongated circular edge 722 defines a portion of the air gap 510 (FIG. 5A) at the front side 701. In an embodiment (not shown), the base 710 provides chassis mounts for attaching the receptacle 501 (FIGS. 5A-B) to a monitor.

As shown in FIGS. 8A-D, the receptacle outer core 800 houses the coil, inner core and contact set and defines a portion of the receptacle core air gap 510 (FIG. 5A). The outer core 800 has a tubular housing 810 defining a back side 802 and a tubular edge 820 extending from the housing 810 and defining a front side 801. Both the housing 810 and the edge 820 have elongated circular cross-sections, with the edge 820 cross-section having a smaller circumference than the housing 810 cross-section. The edge 820 also defines a portion of the air gap 510 (FIG. 5A).

As shown in FIGS. 9A-D, the receptacle contact set 900 has a front side 901, a back side 902, a socket block 910 and corresponding contacts (not visible). The socket block 910 has a generally rectangular cross-sectioned body 910 and generally circular mounting ears 920 extending from the block sides. The ears have ear holes 922 that accept fasteners. The socket block 910 also has several rows of apertures 912 that extend from the front side 901 to the back side 902. Conductive contacts (not visible) are disposed within the apertures 912 and are configured to mate with corresponding plug pins 1130 (FIGS. 11A-D), described below. The receptacle contact set 900 mounts within the inner core 700 (FIGS. 7A-D) so that the mounting ears 920 rest on the core bracket 730 (FIGS. 7A-D). The contact set 900 is attached to the inner core 700 (FIGS. 7A-D) with fasteners disposed through the ear holes 922 and mounting holes 732 (FIGS. 7A-D).

As shown in FIGS. 10A-D, the plug core 1000 mounts the plug contact set 1100 (FIGS. 11A-D) and defines an anchor 550 (FIG. 5B) that releasably locks within the receptacle air gap 510 (FIG. 5A). The plug core 1000 has a tubular housing 1010 defining a back side 1002 and a tubular edge 1020 extending from the housing 1010 and defining a front side 1001. The edge 1020 has an elongated, circular cross-section. The housing 1010 has an elongated, circular cross-section near the front side 1001 and a circular cross-section near the back side that accommodates a cable (not shown). Inside the housing 1010 is a bracket 1030 and corresponding bracket holes 1032 for mounting the plug contact set 1100 (FIGS. 11A-D). A cable aperture 1040 provides cable entry for wiring access to the plug contact set 1100 (FIGS. 11A-D) via the back side 1002. The elongated circular edge 1020 defines the anchor 550 (FIG. 5B) at the front side 1001.

As shown in FIGS. 11A-D, the plug contact set 1100 has a front side 1101, a back side 1102, a pin block 1110 and corresponding pins 1130. The pin block 1110 has a generally rectangular cross-sectioned body having generally circular mounting ears 1120 extending from the block sides. The ears 1120 have ear holes 1122 that accept fasteners. The pin block 1110 also has several rows of apertures 1112 that extend from the front side 1101 to the back side 1102. Conductive pins 1130 are disposed within the apertures 1112 and are configured to mate with corresponding receptacle contacts, described above. The contact set 1100 mounts within the plug core 1000 (FIGS. 10A-D) so that the mounting ears 1120 rest on the core bracket 1030 (FIGS. 10A-D). The contact set 1100 is attached to the receptacle core 1000 (FIGS. 10A-D) with fasteners disposed through the ear holes 1122 and mounting holes 1032 (FIGS. 10A-D).

A magnetic connector has been disclosed in detail in connection with various embodiments. These embodiments are disclosed by way of examples only and are not to limit the scope of the claims that follow. One of ordinary skill in art will appreciate many variations and modifications.

What is claimed is:
1. A magnetic connector comprising:
a first magnetic element;
a second magnetic element;
a first contact set housed proximate the first magnetic element;
a second contact set housed proximate the second magnetic element;
at least one of the magnetic elements responsive to a current input so as to alter a magnetic coupling between the magnetic elements;
the magnetic coupling assists in at least one of making and breaking an electrical connection between the first contact set and the second contact set;
wherein the first magnetic element comprises:
a core of magnetically permeable material;

a conductive coil having "N" turns disposed around at least a portion of the core;

a plurality of coil leads in communications with a current source;

an air gap defined within the core; and the current source having "I" amps energizing the coil so as to generate an electromagnetic field within the air gap proportional to N times I.

2. The magnetic connector according to claim 1 wherein the second magnetic element comprises:

an anchor of magnetically permeable material sized to closely fit within the air gap;

the contact sets making an electrical connection as the anchor is manually inserted into the air gap and breaking an electrical connection as the anchor is manually withdrawn from the air gap; and the anchor locking within the air gap in response to a magnetic field within the air gap so as to maintain the electrical connection between the contact sets.

3. The magnetic connector according to claim 2 further comprising:

a switch in series with the coil so as to control coil energization; and an LED in series with the switch so as to indicate coil energization.

4. The magnetic connector according to claim 3 further comprising:

a permanent magnet disposed within the second magnetic element proximate the anchor; and the permanent magnet having poles oriented so that the permanent magnet field opposes the air gap field.

5. The magnetic connector according to claim 4 further comprising:

a permanent magnet disposed within the first magnetic element proximate the air gap; and the permanent magnet having poles oriented so that the permanent magnet field opposes the air gap field.

6. A magnetic connector method for interconnecting an optical sensor and a physiological monitor, the magnetic connector having a monitor receptacle and a cable plug, the magnetic connector method comprising the steps of:

defining a receptacle core and a plug core each comprising a magnetically permeable material;

defining a plug core comprising a magnetically permeable material;

housing receptacle contacts within the receptacle core;

housing plug contacts within the plug core;

interconnecting the receptacle core and the plug core so as to electrically connect the receptacle contacts and the plug contacts; and magnetically coupling the receptacle core and the plug core so as to maintain the interconnection;

wherein the magnetically coupling further comprises disposing a coil around a first one of the receptacle and the plug cores so as to form an electromagnet; and wherein the magnetically coupling further comprises:

disposing an air gap in the first one of the cores; and extending an anchor from a second one of the cores.

7. The magnetic connector method according to claim 6 wherein the magnetically coupling further comprises:

magnetically locking the anchor within the air gap.

8. The magnetic connector method according to claim 7 wherein the magnetically coupling further comprises switching current to the coil so as to unlock the anchor from the air gap.

9. The magnetic connector method according to claim 8 wherein the magnetic coupling further comprises embedding at least one permanent magnet within one of the cores.

10. The magnetic connector method according to claim 9 wherein the magnetic coupling further comprises:

embedding at least one permanent magnet proximate the anchor;

the switching comprising energizing the coil so as to create an opposing field to the permanent magnet within the air gap.

11. The magnetic connector method according to claim 10 wherein the magnetic coupling further comprises:

embedding at least one permanent magnet proximate the air gap;

the switching comprising energizing the coil so as to create an opposing field to the permanent magnet within the air gap.

* * * * *